United States Patent [19]
Tabiti et al.

[11] Patent Number: 5,888,746
[45] Date of Patent: Mar. 30, 1999

[54] TUMOR DIAGNOSIS AND PROGNOSIS

[75] Inventors: Karim Tabiti; Catherine Jane Pallen, both of Ridge Crescent, Singapore

[73] Assignee: Institute of Molecular and Cell Biology, Singapore, Singapore

[21] Appl. No.: 750,352
[22] PCT Filed: Jun. 6, 1995
[86] PCT No.: PCT/EP95/02166
  § 371 Date: Mar. 10, 1997
  § 102(e) Date: Mar. 10, 1997
[87] PCT Pub. No.: WO95/34818
  PCT Pub. Date: Dec. 21, 1995

[30] Foreign Application Priority Data

Jun. 10, 1994 [GB] United Kingdom .................. 9411671

[51] Int. Cl.⁶ .................................................. G01N 33/53
[52] U.S. Cl. ............................ 435/7.1; 435/6; 435/7.7; 435/7.9; 435/7.91; 435/7.92; 435/7.93; 435/7.94; 435/7.95; 435/40.5; 435/960
[58] Field of Search .............................. 435/7.1, 6.6, 7.7, 435/7.9–7.95, 960, 40.5, 40.52

[56] References Cited

U.S. PATENT DOCUMENTS 5,538,886 7/1996 Schlessinger et al. .................. 435/330

FOREIGN PATENT DOCUMENTS

WO A 94 01119 1/1994 WIPO .

OTHER PUBLICATIONS

Seminars in Cell Biology, vol. 4, 1993 pp. 403–408, C.J. Pallen "The receptor–like protein tyrosine phsphatase alpha: a role in cell proliferation and oncogenesis".

The Journal of Biological Chemistry, vol. 269, No. 3, 21 Jan. 1994 pp. 2075–2081, T. Matozaki et al., "Molecular cloning of a human transmembrane–type protein tyrosine phosphatase and its expression in gastrointestinal cancers".

Cancer Letters, vol. 93, No. 2, 13 Jul. 1995 pp. 239–248, K. Tabiti et al., "Increased mRNA expression of the receptor–like protein tyrosine phosphatase alpha in late stage colon carcinomas".

Letters to Nature, vol. 346, 23 Aug. 1990, pp. 756–760, A.C. Schuh et al., "obligatory wounding requirement for tumorigenesis in v–jun transgenic mice".

*Primary Examiner*—Sheela Huff
*Attorney, Agent, or Firm*—Nixon & Vanderhye

[57] ABSTRACT

A method for diagnosis or prognosis of a cancer is disclosed. The method comprises (i) detecting in a first biological sample protein tyrosine phosphate α (PTPα) or PTPα nucleic acid, and (ii) comparing the level of PTPα or PTPα nucleic acid in the first sample with the level in a second biological sample known to be from normal tissue. Any overexpression of PTPα or PTPα nucleic acid in the first sample compared to the second sample is indicative that the first sample is from a cancerous tissue.

7 Claims, 3 Drawing Sheets

TUMOR DIAGNOSIS AND PROGNOSIS

The invention relates to the diagnosis and prognosis of cancers, particularly colorectal carcinomas.

The tumorigenic process leading to colorectal carcinoma formation involves multiple genetic alterations (Fearon et al (1990) Cell 61, 759–767). Tumor suppressor genes such as p53, DCC and APC are frequently inactivated in colorectal carcinomas, typically by a combination of genetic deletion of one allele and point mutation of the second allele (Baker et al (1989) Science 244, 217–221; Fearon et al (1990) Science 247, 49–56; Nishisho et al (1991) Science 253, 665–669; and Groden et al (1991) Cell 66, 589–600). Recently, mutation of two mismatch repair genes which regulate genetic stability was associated with a form of familial colon cancer (Fishel et al (1993) Cell 75, 1027–1038; Leach et al (1993) Cell 75, 1215–1225; Papadopoulos et al (1994) Science 263, 1625–1629; and Bronner et al (1994) Nature 368, 258–261). Proto-oncogenes such as myc and ras are altered in colorectal carcinomas, with c-myc RNA being overexpressed in as many as 65% of carcinomas (Erisman et al (1985) Mol. Cell. Biol. 5, 1969–1976), and ras activation by point mutation occurring in as many as 50% of carcinomas (Bos et al (1987) Nature 327, 293–297; and Forrester et al (1987) Nature 327, 298–303). Other proto-oncogenes, such as myb and neu are activated with a much lower frequency (Alitalo et al (1984) Proc. Natl. Acad. Sci. USA 81, 4534–4538; and D'Emilia et al (1989) Oncogene 4, 1233–1239). No common series of genetic alterations is found in all colorectal tumors, suggesting that a variety of such combinations may be able to generate these tumors.

Increased tyrosine phosphorylation is a common element in signalling pathways which control cell proliferation. The deregulation of protein tyrosine kinases (PTKS) through overexpression or mutation has been recognized as an important step in cell transformation and tumorigenesis, and many oncogenes encode PTKs (Hunter (1989) in oncogenes and the Molecular Origins of Cancer, ed. Weinberg (Cold Spring Harbor Laboratory Press, Cold Spring Harbor, N.Y.), pp. 147–173). Numerous studies have addressed the involvement of PTKs in human tumorigenesis. Activated PTKs associated with colorectal carcinoma include c-neu (amplification), trk (rearrangement), and c-src and c-yes (mechanism unknown) (D'Emilia et al (1989), ibid; Martin-Zanca et al (1986) Nature 3, 743–748; Bolen et al (1987) Proc. Natl. Acad. Sci. USA 84, 2251–2255; Cartwright et al (1989) J. Clin. Invest. 83, 2025–2033; Cartwright et al (1990) Proc. Natl. Acad. Sci. USA 87, 558–562; Talamonti et al (1993) J. Clin. Invest. 91, 53–60; and Park et al (1993) Oncogene 8, 2627–2635).

Obviously, protein tyrosine phosphatases (PTPs) are also intimately involved in regulating cellular phosphotyrosine levels. The growing family of PTPs consists of non-receptor and receptor-like enzymes (for review see Charbonneau et al (1992) Annu. Rev. Cell. Biol. 8, 463–493; and Pot et al (1992) Biochim. Biophys. Acta 1136, 35–43). All share a conserved catalytic domain, which in the non-receptor PTPs is often associated with proximal or distal sequences containing regulatory elements directing protein-protein interaction, intracellular localization, or PTP stability. The receptor like PTPs usually contain two catalytic domains in their intracellular region, and in addition have a transmembrane region and heterogeneous extracellular regions. The extreme diversity of the extracellular region, compared to the relatively conserved intracellular portion of these enzymes, suggests that these PTPs are regulated by specific extracellular factors, few of which have been identified. Some PTPs can act in opposition to PTKS. For example, the nonreceptor PTP 1B and TC-PTP can reverse or block cell transformation induced by the oncogenic tyrosine kinases neu or v-fms, while another non-receptor PTP (known as 3HC134, CL100, HVH1, PAC-1, erp, or MKP-1) can reverse the PTK-mediated activation of a central signalling enzyme, MAP kinase (Brown-Shimer et al (1992) Cancer Res. 52, 478–482; Zander et al (1993) Oncogene 8, 1175–1182; Sun et al (1993) Cell 75, 487–493; and Ward et al (1994) Nature 367, 651–654). Conversely, other PTPs can act in conjunction with PTKs. Two receptor-like PTPs, PTPα and CD45, respectively activate the tyrosine kinases c-src or lck and fyn while the non-receptor SH-PTP2 (PTP 1D, PTP-2C, Syp) positively transduces a mitogenic signal from the PDGF receptor tyrosine kinase to ras (WP 94/01119; Zheng et al (1992) Nature 359, 336–339; den Hertog et al (1993) EMUB J. 12, 3789–3798; Mustelin et al (1989) Proc. Natl. Acad. Sci. USA 86, 6302–6306; Ostergaard et al (1989) Proc. Natl. Acad. Sci. USA 86, 8959–8963; Cahir McFarland et al (1989) Proc. Natl. Acad. Sci. USA 90, 1402–1406; and Li et al (1994) Mol. Cell. Biol. 14, 509–517).

Very few studies have examined alterations in PTP expression or activity that may be associated with tumorigenesis. As indicated above, two PTP-related mechanisms, either the inactivation or the overactivation of a PTP, could increase cellular phosphotyrosine levels and result in uncontrolled cell proliferation and tumorigenesis. In relation to PTP inactivation, it is of interest that the gene encoding receptor-like PTP7 is situated on a region of chromosome 3 that is often lost in renal and lung carcinomas, and that a PTPW allele is lost in some renal carcinoma and lung carcinoma cell lines (LaForgia et al (1991) Proc. Natl. Acad. Sci. USA 88, 5036–5040). As regards PTP overactivation, it has been shown that when PTPα is overexpressed in rat embryo fibroblasts, cell transformation occurs and the cells are tumorigenic in nude mice (WO 94/01119 and Zheng et al (1992), ibid). PTPα is a receptor-like enzyme with a short, unique extracellular domain and two tandem catalytic domains (WO 92/01050; Matthews et al (1990) Proc. Natl. Acad. Sci. USA 87, 4444–4448; Sap et al (1990) Proc. Natl. Acad. Sci. USA 87, 6112–6116; and Krueger et al (1990) EMBO J. 9, 3241–3252). Compared to many other receptor-like PTPs with a restricted and lineage-specific expression, PTPα is widely expressed (Sap et al (1990), ibid and Krueger et al (1990), ibid).

We have now found that the level of PTPα expression is increased in significant numbers of tumors and that PTα can therefore be used as a marker for the diagnosis or prognosis of cancers. Accordingly, the invention provides a method for diagnosis or prognosis of a cancer, which method comprises detecting in a biological PTPα or PTPα nucleic acid.

In general, the level of PTPα or PTPα nucleic acid in a first biological sample derived from tissue suspected of being neoplastic or potentially neoplastic is compared with the level in a second (control) biological sample derived from normal tissue. The first and second biological samples may be derived from the same subject or from different subjects. The second (control) biological sample may be derived from a pool of normal tissue; this would help to eliminate or define variation in PTPα expression between individual subjects. In the case of colorectal carcinoma, the second biological sample is suitably derived from normal colon mucosa at least 5 cm distant from the tissue suspected of being neoplastic or potentially neoplastic.

If the level of PTPα or PTPα nucleic acid is increased in the first sample compared to the second sample, this indicates that the first sample is indeed derived from a tissue which is neoplastic or potentially neoplastic. Typically, an increase of from 1.5- to 20-fold, more typically from 2- to 10-fold or 6- to 10-fold, is indicative that a tissue is neoplastic or potentially neoplastic. The level of PTPα or PTPα nucleic acid is generally normalised with respect to the level of a protein or nucleic acid expressed at the same level in normal, neoplastic and potentially neoplastic tissues. For example, the level of PTPα mRNA may be normalised with respect the level of 18S ribosomal RNA or β-actin mRNA.

A "potentially neoplastic tissue" is a tissue which contains a genetic alteration that increases the probability of the tissue becoming neoplastic. A "normal tissue" is a tissue which is neither neoplastic nor potentially neoplastic.

The method of the invention may be used for diagnosis or prognosis of a number of different types of cancer. The cancer is generally a cancer in which the tumor exhibits an elevated level of src family kinase activity (e.g. an elevated level of $pp60^{c-src}$ kinase activity). The cancer may, for example, be a colorectal carcinoma, a neuroblastoma or a breast carcinoma. The invention is particularly useful for detecting a colorectal carcinoma. The invention could be used to detect metastases; c-src is reportedly very high in colorectal metastases and PTPα may be correspondingly elevated. The invention may be of a good indicator/ prognosticator of patient survival and development of metastases.

PTPα may be used in combination with other diagnostic and prognostic markers of a cancer in order to achieve a higher level of reliability. We found that 10 out of 14 (70%) advanced colorectal carcinomas tested exhibited elevated levels of PTPα mRNA. Other suitable markers of colorectal carcinoma include c-myc RNA which is overexpressed in 65% of carcinomas and ras activation by point mutation which occurs in 50% of carcinomas. Other proto-oncogenes such as myb and neu are activated with a much lower frequency.

The PTPα or PTPα nucleic acid detected according to the invention may be a normal (unmutated) PTPα or PTPα nucleic acid, or a mutant PTPα or PTPα nucleic acid. Detection of mutant PTPα or PTPα nucleic acid is important in cases in which overexpression of PTPα is caused by a mutation in the PTPα gene. The PTPα nucleic acid may be any nucleic acid encoding PTPα, and will usually be PTPαmRNA or PTPαDNA.

A variety of types of assay may be used to detect PTPαor PTPα nucleic acid in the method of the invention. The assay is preferably quantitative. The PTPα or PTPα nucleic acid may be detected in situ in a tissue sample or in a sample of isolated cellular material (e.g. cellular nucleic acid or cellular protein).

In situ detection may be accomplished by removing a histological sample from a patient and allowing a labelled binding protein (e.g. a labelled antibody) or a labelled nucleic acid probe to bind or hybridize to PTPα or PTPα nucleic acid respectively. Through use of such a procedure, it is possible not only to detect PTPα or PTPα nucleic acid but also to determine its spatial distribution. Detection in a sample of isolated cellular material may be carried out using techniques such as Southern/Northern/Western blotting, ELISA (enzyme-linked immunoassay), RNA protection assay and dot blot hybridization.

A biological sample used according to the invention may be a tissue sample, a biological fluid (e.g. blood or saliva), fecal material or a sample of isolated cellular material (e.g. cellular nucleic acid or cellular protein). A tissue sample may be prepared by conventional histological techniques and a sample of isolated cellular material may be prepared by conventional purification techniques. Fecal material is particularly useful for detection of colon carcinomas because sloughed off colon cells are present in feces. A biological sample is usually derived from a human or animal subject suspected of having cancer, but may be derived from a healthy subject.

The PTPα nucleic acid may be detected with an oligonucleotide probe which hybridizes to the nucleic acid. A probe is a labelled oligonucleotide (usually DNA or RNA) which hybridizes to a part or the whole of the PTPα nucleic acid. A probe is generally at least 10 nucleotides in length, for example from 12 to 100 nucleotides in length. The probe should preferably specifically hybridize to PTPα nucleic acid only and not to other nucleic acids. For example, the sequence of the probe may be chosen so as to hybridize to a portion of PTPα nucleic acid corresponding to the extracellular domain of the protein because the extracellular domain of the protein is unique. A suitable probe is one which hybridizes to nucleotides 369 to 426 of the human PTPα coding sequence.

A probe can be used in a number of types of PTPα nucleic acid detection assay, for example in situ hybridization, RNA protection, Southern or Western blotting and dot blot hybridization. Such assays generally comprise the following steps:

(a) contacting the probe with the biological sample; and (b) detecting probe hybridized with any PTPα nucleic acid present in the sample.

In situ hybridization typically involves contacting a probe with a tissue sample, washing away non-hybridized probe and detecting hybridized probe.

An RNA protection assay typically involves contacting an RNA probe with isolated cellular material, digesting non-hybridized single stranded probe and detecting remaining probe.

Blotting typically involves subjecting isolated cellular material to gel electrophoresis to separate nucleic acids in the material, transferring the separated nucleic acids to a solid support (e. a nitrocellulose support) by blotting, contacting a probe with the separated nucleic acids on the support and detecting the probe.

The PTPα nucleic acid may be amplified before detection. Amplification may be carried out in situ in a tissue sample or in a sample of isolated cellular material. It is possible to detect the amplificant nucleic acid directly by using a labelled primer, a labelled deoxyribonucleoside triphosphate (dNTP) or a labelled ribonucleoside triphosphate (NTP) in the amplification reaction. A number of methods are now known for the amplification of nucleic acid sequences. These include the polymerase chain reaction (PCR), the reverse transcription-polymerase chain reaction (RT-PCR), the self-sustained sequence replication reaction (3SR) and the ligase chain reaction. RT-PCR is described by Kawasaki (1990) Amplification of RNA, in Innis et al Eds, PCR Protocols: A Guide to Methods And Applications, New York, Academic Press; 21–27. RT-PCR using a thermostable recombinant *Thermus thermophilus* (rTth) DNA polymerase is described in Wang et al (1989) Proc. Natl. Acad. Sci. USA 86:9719–9721, and the Perkin-Elmer Biotechnology Products Catalogue, Branchburg, N.J., USA (1993) p.25. 3SR is described by Gingeras et al (1991) Journal of Infectious Diseases 164, 1066–1074 and Gingeras et al (1993) Hepatology 17, 344–346. The ligase chain reaction is described by Barany in PCR Methods and Applications, Cold Spring Harbor Laboratory Press (1991) 1, 5–16. Quantitative RT-PCR may be a particularly useful method for detecting overexpression of PTPα mRNA.

PTPα may be detected with a chemical or biological ligand (e.g. a binding protein or peptide) specific for PTPα. The binding protein is suitably an immunoglobulin, but may also be a naturally occurring protein such as an extracellular matrix protein or a cell surface protein. The immunoglobulin may either be a complete antibody or an antibody fragment having at least one binding site for PTPα. An antibody fragment may be a Fab, F(ab')$_2$, Fv or scFv fragment. The immunoglobulin may be humanised, for example as disclosed in EP-A-239 400 (Winter). A suitable antibody is described in WO 92/01050. The immunoglobulin may be labelled.

The immunoglobulin may be produced using known techniques. For example, monoclonal antibody may be produced from hybridoma cells using the technique first described in Kohler and Milstein (1975) Nature 256, 495–497. Recombinant antibodies and antibody fragments may be produced using the technique described in EP-A-324 162 (Skerra and Pluckthun).

An immunoglobulin may be used to detect PTPα with a number of different assay techniques, for example in situ hybridization, Western blotting and ELISA (enzyme-linked immunoassay). Such techniques generally involve the steps of (a) contacting a biological sample with an immunoglobulin; and (b) detecting immunoglobulin bound to PTPα.

In situ hybridization typically involves contacting an immunoglobulin with a tissue sample, washing away unbound immunoglobulin and detecting bound immunoglobulin.

Western blotting generally involves subjecting isolated cellular material to gel electrophoresis to separate proteins in the material, transferring the separated proteins to a solid support (e.g. a nitrocellulose support) by blotting, contacting an immunoglobulin with the separated proteins on the support and detecting bound immunoglobulin.

ELISA typically involves immobilizing on a solid support an unlabelled antibody specific for PTPα, adding a biological sample so that any PTPα present in the sample is captured by the unlabelled antibody, adding an enzymatically labelled antibody specific for PTPα and detecting bound labelled antibody.

PTPα may also be detected using a direct enzymatic assay of the tyrosine phosphatase activity of PTPα. This could be quantitated by immunoprecipitating PTPα from the biological sample with PTPα antibody, and assaying the immunocomplex for tyrosine phosphatase activity. Such an assay is described in Zheng et al (1992) Nature 359, 336–339.

A number of types of label may be employed to detect PTPα or PTPα nucleic acid. The label may be present on a PTPα binding protein (e.g. an immunoglobulin), a chemical ligand for PTPα, an oligonucleotide probe, a primer, a dNTP or an NTP. Examples of suitable labels include radioactive labels (e.g. $^{35}$S or $^{32}$p), biotin (which may be detected with avidin or streptavidin conjugated to peroxidase), fluorescent labels (e.g. fluorescein), enzymes (e.g. horseradish peroxidase) or digoxigenin. Methods for detecting these labels are well-known.

The invention further provides a kit for diagnosis or prognosis of a cancer, which kit comprises an immunoglobulin specific for PTPα, or an oligonucleotide probe or primer specific for PTPα nucleic acid. The immunoglobulin may be provided on a solid support.

The kit generally also comprises means for detecting the immunoglobulin, probe or primer. The means for detection may be a label on the immunoglobulin, probe or primer specific for PTPα or PTPα nucleic acid. Alternatively, in the case of a kit comprising an immunoglobulin specific for PTPα, the means for detecting binding may be a labelled secondary immunoglobulin reactive with the immunoglobulin specific for PTPα.

The kit may be an ELISA kit, a blotting kit, an in situ hybridization kit, an RNA protection assay kit or a nucleic acid amplification kit. Accordingly, the kit may contain the reagents necessary to detect PTPα or PTPα nucleic acid by each of these techniques as described above. The kit may also comprise a positive or negative control.

The following Examples illustrate the invention.

EXAMPLES

MATERIALS AND METHODS

Figure 1:
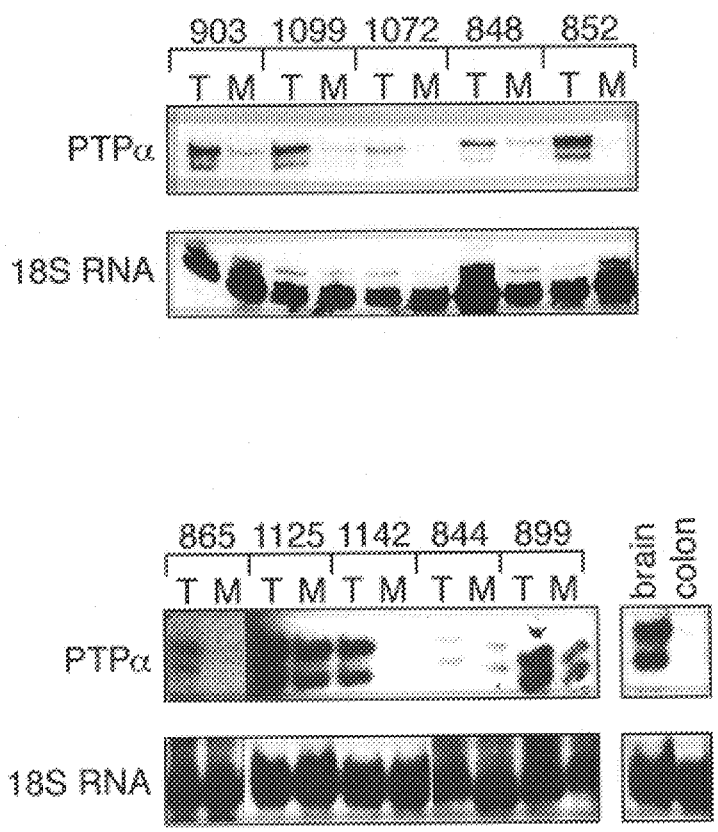
FIG. 1: Expression of PTPα in colorectal tumor and colon mucosa samples determined by RNase protection assay. Total cellular RNA from paired Dukes' D stage colon tumors (T) and adjacent colon mucosa (M), or from rat brain and colon, was mixed and annealed with the labelled PTPα or 18S RNA riboprobes as described in Materials and Methods. After digestion with RNases and gel electrophoresis, protected fragments were visualized by autoradiography. The patient reference number is shown above each pair of tumor and mucosa samples.

Tissue samples. Normal colon mucosal tissue and colon adenocarcinomas were separated from underlying muscle tissue by blunt dissection. The tissues were snap frozen in liquid nitrogen and stored at −80° C. until use. Histopathologic examination, staining, and staging according to the modified Dukes classification (Turnbull et al (1967) Ann. Surg. 16, 420–427) was performed on all tissues by a pathologist. The clinical and histopathological data are shown in Table 1.

Isolation of total cellular RNA. Total cellular RNA was isolated from frozen surgical specimens according to the acid-guanidium isothiocyanate extraction method of Chomezynski and Sacchi (1987) Analyt. Biochem 162, 156–159. RNA integrity was checked by running the RNA on an agarose gel followed by visualization of the 28S and 18S with ethidium bromide.

RNase protection assay. The PTPα probe was constructed by inserting a Bgl II-Pst I PCR fragment coding for the entire extracellular domain of PTPα (bp 1-426) into a pSP73 transcription vector. The plasmid was linearized at a unique Eco R1 site at position 369 of the insert. The resulting riboprobe protects 57nt and 55nt PTPα mRNA fragments corresponding to complementary DNA nt 369 to 426 and an undefined slightly shortened form of this CDNA sequence, respectively. 18S RNA and human β-actin riboprobes were used as internal controls. The pT7 RNA 18S antisense control template contains an 82 bp fragment of a highly conserved region of the human 18S ribosomal RNA gene and was purchased from Ambion. The human β-actin probe was constructed by inserting a 164 bp Pst I-Cla I PCR fragment amplified from human fibroblast cDNA into a pSP72 vector. The riboprobe protects a stretch of 138 nt corresponding to amino acid residues 80 to 126 of β-actin.

Labelled antisense riboprobes were transcribed in the presence of [a-$^{32}$p]rUTP or [a-$^{33}$P]rUTP using the Riboprobe Gemini transcription system (Trade Name, Promega) and purified on a denaturing acrylamide gel. The RNase protection assay was performed as described (Gilman (1994) in Current Protocols in Molecular Biology, eds. Ausubel et al (Current Protocols New York, N.Y.) pp 4.7.1–4.7.6). Equal amounts of total RNA from each pair of tumor and the corresponding mucosa (6–20 μg) were hybridized with labelled riboprobes at 45° C. overnight and the digestion was carried out with a mixture of RNase A (0.05 μg/gl) and RNase T1 (80 units/ml) at 25° C. for one hour. The samples were electrophoresed on a 12% denaturing acrylamide gal and autoradiographed at 70° C. Quantitation and normalization to the internal control was performed with a phosphorimager (Molecular Dynamics) using the Image Quant (Trade Name) program.

Non-radioactive in situ. Non-radioactive in situ hybridization was performed with digoxigenin-labelled sense and antisense PTPα probes. The transcripts represent run off transcripts of the above mentioned construct containing the first 426 nucleotides of PTPα cloned into a pSP73 vector (Promega). However, linearization of the plasmids was achieved with either Bgl II (antisense) or Pst I (sense) digestion. Run off procedures with digoxigenin-11-uridine-5'-triphosphate (DIG-UTP) (Boehringer Mannheim, cat. no. 1209266) and subsequent purification was performed according to the manufacturer's instructions. Integrity and concentration of probes were determined by adding tracer amounts of [a-$^{32}$P] rUTP to the transcription reactions and subsequent visualization of the probes by 6% PAGE and autoradiography.

Fixation of sample tissue, hybridization and detection of digoxigenin-labelled probes was done using conditions specified by the manufacturer (Boehringer Mannheim: Non-radioactive In Situ Hybridization Application Manual) with slight modifications. Briefly, fresh frozen sections (10 μm) of tumor and the corresponding mucosa tissues were fixed in fresh picric acid paraformaldehyde (PAF) for 30 min and subsequently digested with 2 μg/ml Proteinase K for 5 min at 37° C. The digestion was stopped by rinsing sections in 0.2% glycine. After postfixing with chloroform, the sections were rehydrated and prehybridized in HB buffer (50% (v/v) deionized formamide, 4× SSC, 500 μg/ml sheared ssDNA, 5 mg/ml yeast t-RNA, 1× Denhardt's solution and 10% (w/v) dextran sulfate in DEPC-treated dH$_2$O) for 3 h at 55° C. Hybridization with saturating amounts of antisense and sense PTPα probe in the same buffer was allowed to occur overnight at 55° C. After hybridization, non-specifically bound RNA probe was removed by washing the sections twice with 2× SSC, once with 0.2× SSC and twice with 0.1× SSC. All washes were carried out at 45° C. for 15 min each. Prior to the immunohistochemical detection of RNA—RNA hybrids with peroxidase-coupled anti-digoxigenin-POD Fab fragments (Boehringer Mannheim, cat. no. 1207733), endogenous peroxidase activity was removed from the sample tissues by treating the sections with 0.03% H$_2$O$_2$. Preblocked sections (PBS=1% BSA [Fraction V]+0.1% Tween 20) were incubated with a 1:100 dilution of peroxidase-coupled anti-digoxigenin-POD Fab fragments for 30 min at 37° C. The digoxigenin-antibody complex was then visualised using diaminobenzidine as the chromogen. Sections were counterstained with neutral red.

RESULTS

Figure 2:
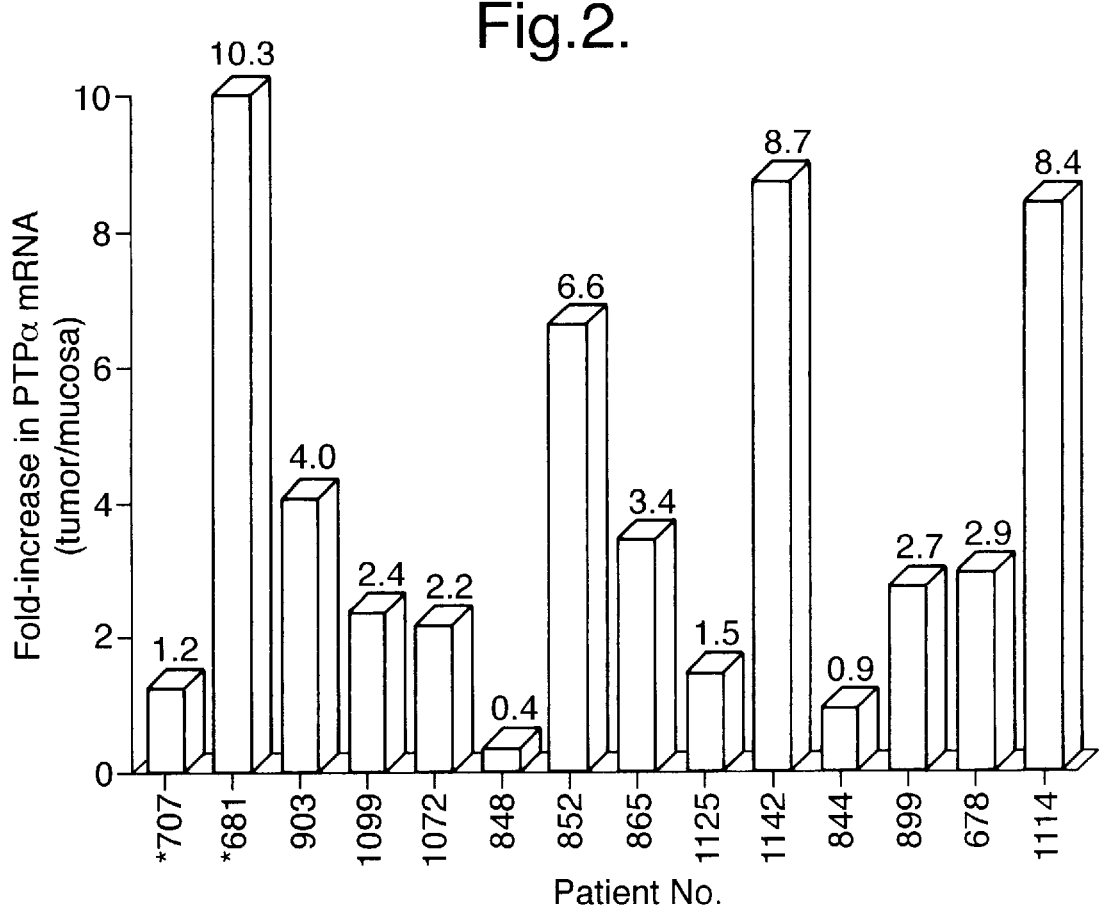
FIG. 2: Fold-increase of PTPα mRNA in colon tumors compared to colon mucosa. The PTPα and 18S RNA protected fragments detected by RNase protection analysis were quantitated using a phosphorimager. The PTPα signals were normalized by calculating the ratio of PTPα mRNA to 18S RNA within each sample. The fold-increase in PTPα mRNA in tumors compared to mucosa was calculated by dividing the normalized tumor PTPα mRNA units by the normalized mucosa PTPα mRNA units for each pair of samples from one patient. The calculated fold-increase is shown numerically above each bar. Two samples where the β-actin signal (instead of the 18S RNA signal) was used for normalization, and quantitation was performed by densitometric scanning with a Visage 2000 Image analysis system (Trade Name, BioImage Products), are marked with an asterisk. Patient reference numbers are shown along the bottom of the graph.

Elevation of PTPα mRNA level in human colon carcinomas. Expression of human receptor-like PTPα in primary colorectal carcinomas was examined at the mRNA level using RNase protection assays. Total RNA was prepared from 14 tumors classified according to Dukes' staging as stage D. By definition, these primary lesions have given rise to distant metastases. We selected only D stage primary tumors for analysis since we reasoned that any late occurring changes in PTPα expression would be detectable at this point, and to minimize sample heterogeneity as much as possible. The PTPα mRNA level in any one tumor was compared to that in an adjacent (at least 5 cm distant) normal colon mucosa sample. Sample RNA was hybridized with a radiolabeled probe spanning nucleotides 369–426 of human PTPα cDNA. This corresponds to a portion of the extracellular region of PTPα and was chosen since this region is unique to PTPα, whereas some of the sequence encoding the intracellular region of PTPα is homologous to that encoding a similar portion of receptor-like PTPE (Kruegar et al (1990) EMBO J. 9, 3241–3252). The results of RNase protection assays on 10 paired samples are shown in FIG. 1. Two protected PTPα fragments of 57 and 55 nucleotides are consistently detected in tumors and adjacent mucosa. The sum of both signals was used to quantitate PTPα mRNA level. To normalize the amount of RNA used for the protection assay, samples were probed in parallel with β-actin (not shown) or 18S RNA sequences (FIG. 1). Quantification and normalization of the PTPα and 18S RNA or β-actin protected fragments reveals a greater than 2-fold increase in detectable PTPα mRNA in tumors compared to normal mucosa in 10 of 14 (~72%) of the paired samples. The increase in these ten samples ranged from 2.2- to 10.3-fold (FIG. 2). We cannot at present determine whether this increased steady-state level of PTPα mRNA is due to increased message stability or an increased rate of transcription in the tumor tissue. Samples from four patients (#707, 848,1125,844) showed no increase in tumor PTPα mRNA. Clinical data related to the tumor samples examined are shown in Table 1.

In line with earlier findings that PTPα is expressed to a lower extent in some organs such as lung, heart and stomach as compared to tissues with high expression such as brain, PTPα mRNA is present at low levels in colon (compare rat colon and brain samples, FIG. 1) (Matthews et al (1990) Proc. Natl. Acad. Sci. USA 87, 4444–4448; Sap et al (1990) Proc. Natl. Acad. Sci. USA 87, 6112–6116).

Figure 3A:
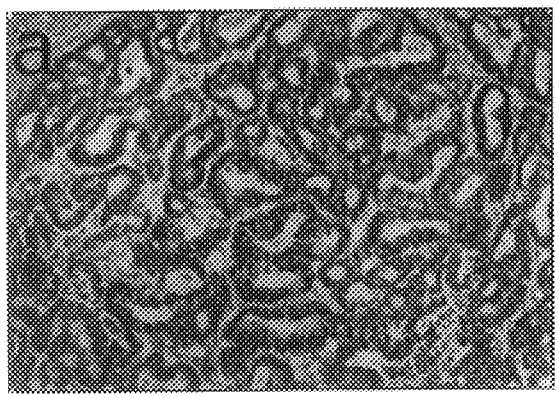
FIG. 3(a–e): In situ hybridization to PTPα mRNA. Colon tumor (a, c, e) and colon mucosa (at least 5 cm distance from the tumor) (b, d) were sectioned and stained with hematoxylin and eosin (a, b), or probed with digoxygenin-labelled anti-sense PTPα RNA (c, d) or sense PTPα RNA (e) and counterstained with neutral red, as described in Materials and methods.
Figure 3B:
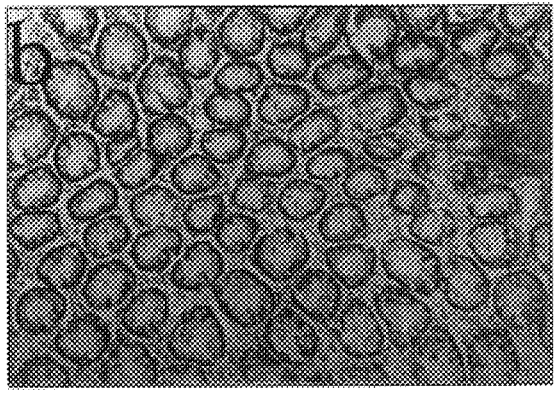
Figure 3C:
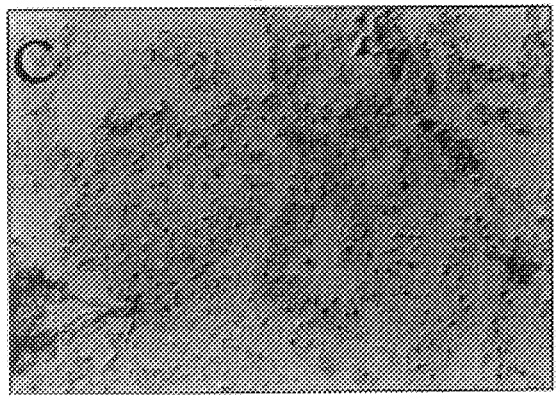
Figure 3D:
Figure 3E:
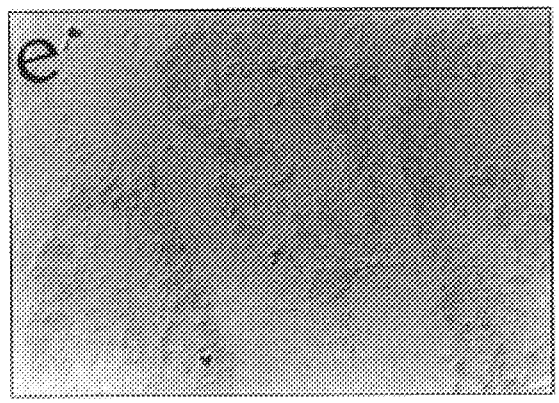

In situ PTPα RNA hybridization in colon carcinoma and colon mucosa tissues. Due to the heterogeneic nature of tumor tissues, non-radioactive in situ RNA hybridization was performed on sections of adenocarcinomas and adjacent mucosa to determine the cells responsible for the overall increase in PTPα expression. FIG. 3a is a representative photomicrograph of a hematoxylin and eosin stained Dukes' stage D tumor showing typical morphological and cytological aberrations, compared to the normal mucosa (FIG. 3b). When neutral red counterstained tumor tissues were probed with digoxigenin-labelled antisense PTPα RNA (FIG. 3c), malignant and transformed epithelial cells showed a strong signal. Neither the surrounding mesenchymal tissue nor the normal mucosa located at least 5 cm away from the neoplasm (FIG. 3d) showed any significant signal, thereby confirming that the increase in PTPα transcripts is confined to the actual neoplastic and transformed epithelial cells. As a control, a section of the same tumor was probed with the mRNA sense strand of PTPα, however, this did not stain any parts of the tissue (FIG. 3e). The strong signal observed in the tumor tissue compared to the colon mucosa (FIGS. 3c and 3d) is consistent with the high increase in PTPα mRNA level detected by RNase protection assays of some of the tumors.

TABLE 1

Clinical patient data.

| Patient | Site | Type | LN involv. | Distant metastases | PTPα mRNA increase (>2X) |
|---|---|---|---|---|---|
| 707 | rectum | adenocarcinoma | + | lung | no |
| 681 | rectum | adenocarcinoma | + | liver/peritoneal | yes |
| 903 | recto-sigmoid | adenocarcinoma | + | liver | yes |
| 1099 | sigmoid | adenocarcinoma | − | liver | yes |
| 1072 | trans-colon | adenocarcinoma | + | liver | yes |
| 848 | hepatic flexure | mucinous adenocarcinoma | − | liver | no |
| 852 | rectum | adenocarcinoma | + | liver | yes |
| 865 | des-cending colon | adenocarcinoma | + | liver | yes |
| 1125 | rectum | adenocarcinoma | + | liver | no |
| 1142 | rectum | adenocarcinoma | + | liver | yes |
| 678 | rectum | adenocarcinoma | + | lung | yes |
| 844 | rectum | adenocarcinoma | + | liver | no |
| 899 | rectum | adenocarcinoma | + | peritoneal | yes |
| 1114 | sigmoid | adenocarcinoma | − | liver | yes |

Clinical data of patients whom Dukes' D stage tumors and mucosa were examined for PTPα mRNA level. Site, site of the primary tumor; type, type of primary tumor; LN involv., lymph node involvement; distant metastases, site(s) of secondary lesions; PTPα mRNA increase, at least a 2-fold increase in PTPα mRNA in tumors compared to mucosa.

CONCLUSION

Numerous investigations have been directed towards uncovering the molecular events leading to malignant transformation. In the present study, we have explored the possible involvement of PTPα in cancer. Our results demonstrate, for the first time, increased steady-state levels of a specific receptor-like PTP mRNA in tumors. Overexpression of PTPα occurs with high frequency in Dukes' D stage human colon carcinoma. In 10 of 14 paired samples (tumor versus normal mucosa), PTPα transcripts were increased between 2- to 10-fold in tumor tissue over adjacent normal mucosal tissue. In four of these 10 cases a particularly high level of PTPα mRNA (>6-fold elevation) was observed in colon tumors compared to normal mucosa. In situ hybridization confirms that increased PTPα mRNA is localized in neoplastic cells of the tumor sample.

We claim:

1. A method for diagnosis or prognosis of a cancer, which method comprises (i) detecting in a first biological sample protein tyrosine phosphatase α (PTPα) or PTPα nucleic acid, and (ii) comparing the level of PTPα or PTPα nucleic acid in the first sample with the level in a second biological sample known to be from normal tissue, wherein any overexpression of PTPα or PTPα nucleic acid in the first sample compared to the second sample is indicative that the first sample is from a cancerous tissue.

2. The method according to claim 1, wherein the second biological sample is from a pool of normal tissue and is obtained by mixing samples from more than one subject.

3. The method according to claim 1, wherein the cancer is a colorectal carcinoma.

4. The method according to claim 1, wherein in step (i) the PTPα or PTPα nucleic acid is detected in situ in a tissue sample.

5. The method according to claim 1, wherein in step (i) the PTPα or PTPα nucleic acid is detected in a sample of isolated cellular protein or isolated cellular nucleic acid.

6. The method according to claim 1, wherein in step (i) the PTPα is detected with an immunoglobulin specific for PTPα.

7. The method according to claim 1, wherein in step (i) the PTPα nucleic acid is detected with an oligonucleotide probe to the nucleic acid.

* * * * *